United States Patent [19]

Grabenkort

[11] Patent Number: 4,784,259

[45] Date of Patent: Nov. 15, 1988

[54] CONTAINER CONSTRUCTION WITH VANED EXTRACTOR

[75] Inventor: Richard W. Grabenkort, Barrington, Ill.

[73] Assignee: Abbott Laboratories, North Chicago, Ill.

[21] Appl. No.: 9,358

[22] Filed: Jan. 30, 1987

[51] Int. Cl.[4] .............................................. A61M 5/14

[52] U.S. Cl. .................................... 206/221; 215/354; 215/356

[58] Field of Search ............... 206/219, 220, 221, 222; 220/307; 215/DIG. 1, 354, 356, DIG. 8; 604/409, 410, 416

[56] References Cited

U.S. PATENT DOCUMENTS

| | | | |
|---|---|---|---|
| 2,526,225 | 10/1950 | Gronemeyer et al. | 215/354 |
| 3,262,599 | 7/1966 | Muller | 220/307 |
| 3,372,833 | 3/1968 | Baranne | 220/307 X |
| 3,450,299 | 6/1969 | Barbera | 220/353 |
| 3,532,372 | 10/1970 | Stroud | 220/307 X |
| 3,809,277 | 5/1974 | Kaltenhauser et al. | 215/354 X |
| 4,024,952 | 5/1977 | Leitz | 206/221 |
| 4,334,632 | 6/1982 | Watanabe | 220/307 |
| 4,432,755 | 2/1984 | Pearson | 604/416 X |
| 4,588,105 | 5/1986 | Schmitz et al. | 220/307 X |
| 4,614,267 | 9/1986 | Larkin | 206/221 |

*Primary Examiner*—David T. Fidei
*Attorney, Agent, or Firm*—Neuman, Williams, Anderson & Olson

[57] ABSTRACT

A flexible diluent container has a vaned port plug which enhances or modifies the mechanical interlock with a stopper of an additive vial in a drug delivery system. The additive vial is screwed into the port of the diluent container with the recess of the vial stopper fitting over the engagement portion of the port plug. In doing so, the vanes or wings of the port plug present a minimal frontal area and hence minimal resistance to passage through the neck of the stopper recess. Also, being flexible, they tend to fold or wrap in against the core of the extractor as the vial and stopper are rotated and advanced into the seated position, thereby further reducing the axial forces involved. Once the port plug is fully seated, the vanes or wings open up to form a lateral shoulder on the inward side of the throat shoulder of the stopper, thus providing good gripping on the port plug when the user wants to manipulate the bag and pull the port plug-stopper combination off for the mixing of the contents of the two compartments through the port.

13 Claims, 3 Drawing Sheets

CONTAINER CONSTRUCTION WITH VANED EXTRACTOR

This invention relates to a dual container system having means to effect sterile intermixing of the contents of the two containers by external manipulation after the containers are joined. More particularly, this invention relates to the design of a cover or port plug which enhances or modifies the mechanical interlock between the vial stopper of an additive container and the port plug of a flexible diluent container thus enhancing the reliability of engagement as well as performing satisfactorily with a wide variety of stopper materials of varying resilience and design.

In particular, this invention is for use in systems involving packaging of a medicament and a diluent in separate containers which may be connected to one another at the time of use for convenient safe mixing of the medicament and diluent. Such container systems are known in the art and currently are sold by Abbott Laboratories of North Chicago, Ill. under the trademark ADD-VANTAGE. A number of embodiments of such systems are disclosed in U.S. Pat. Nos. 4,614,267 to Larkin and 4,614,515 to Tripp and Larkin, both of which are assigned to the assignee of this invention. The disclosures in such patents are incorporated herein by reference.

In the noted system the flexible diluent container includes a tubular port which provides a means for securing thereto a stoppered medicament vial as well as a stopper removal means. The stoppers each have a shouldered recess in their exposed end. Previously the stopper removal means was composed of a truncated cone or mushroom shaped engagement element or extractor which is attached to a removable cover that covers and seals the inner end of the port. As a stoppered vial is advanced into and engaged with the port, normally by threaded interengagement, the vial stopper advances onto the extractor. The extractor thereby engages the stopper to subsequently pull the stopper from the vial when the cover is pulled from the port.

A wide variety of materials of varying hardness or resilience are used to manufacture vial stoppers since governmental approval is required for the type of material to be used with a particular medicament. Stoppers made from softer materials are more susceptible to being pushed into the medicament vial during engagement by the extractor and/or to the extractor pulling out of the stopper during attempted extraction, whereas stoppers made from harder materials are often more difficult to engage. Difficulty of engagement between the vial stopper and port plug and in insuring the subsequent withdrawal of the stopper also is due in part to the wide variety of physical designs of the vial stoppers e.g., tapered or cylindrical. Of course, the axial insertion force must be less than the force which will remove the port plug from the port closing position.

It is highly desirable to provide a diluent container with a port plug which will provide high reliability of engagement into the stoppers of vials despite variations in materials and designs of those stoppers, to avoid pushing the stoppers into the vials and assuring withdrawal of any stopper with the extractor, and which will avoid pushing the cover off of the inner end of the port.

An important feature of this invention is that the port plug has a universal capability of functioning with vial stoppers made from a wide variety of materials and in a wide variety of designs. It provides very high reliability of engagement between the port plug of the flexible diluent container and vial stopper of the additive medicament vial and of subsequent withdrawal of the stopper.

It is therefore an object and advantage of the present invention to afford a diluent container with a port plug which had the aforementioned and other capabilities.

SUMMARY OF THE INVENTION

This invention relates to diluent containers with a new design of a port plug such as to enhance or modify the mechanical interlock to be made between the vial stopper of the additive container and the vial port plug of the flexible diluent container thus providing high or absolute reliability of engagement. This is accomplished by a vaned plug design which requires relatively low force for the port plug to be engaged into the stopper while preserving or increasing the amount of force which can be transmitted for removing the stopper. In this manner the port fluid seal is maintained while the additive vial is engaged into the port of the flexible diluent container and the vial stopper becomes reliably engaged to the port plug of the flexible diluent container. This, in turn, enables the user to manipulate the bag and pull the stopper from the attached vial by pulling the port plug inwardly off the port, thus resulting in the mixing of the contents of the two compartments through the port. Normally this involves dumping of the contents of the vial into the diluent in the bag.

In the particular design of this invention the medicament vial typically is screwed into the port of the diluent container with the recess of the vial stopper fitting over the engagement portion of the port plug. In doing so, the vanes or wings of the port plug present a minimal frontal area and hence minimal resistance to passage through the neck of the stopper recess. Also, being flexible, they tend to fold or wrap in against the core of the extractor as the vial and stopper are rotated and advanced into the seated position, thereby further reducing the axial forces involved. Once the port plug is fully seated the vanes or wings open up to form a lateral shoulder on the inward side of the throat shoulder of the stopper thus providing good gripping on the port plug when the user wants to manipulate the bag and pull the port plugstopper combination.

DESCRIPTION OF THE DRAWINGS

A better understanding of the mechanical interlock to be made between the vial stopper of the additive container and the port plug of the flexible container will be had by reference to the drawings wherein.

DESCRIPTION OF PREFERRED EMBODIMENT

Figure 1:
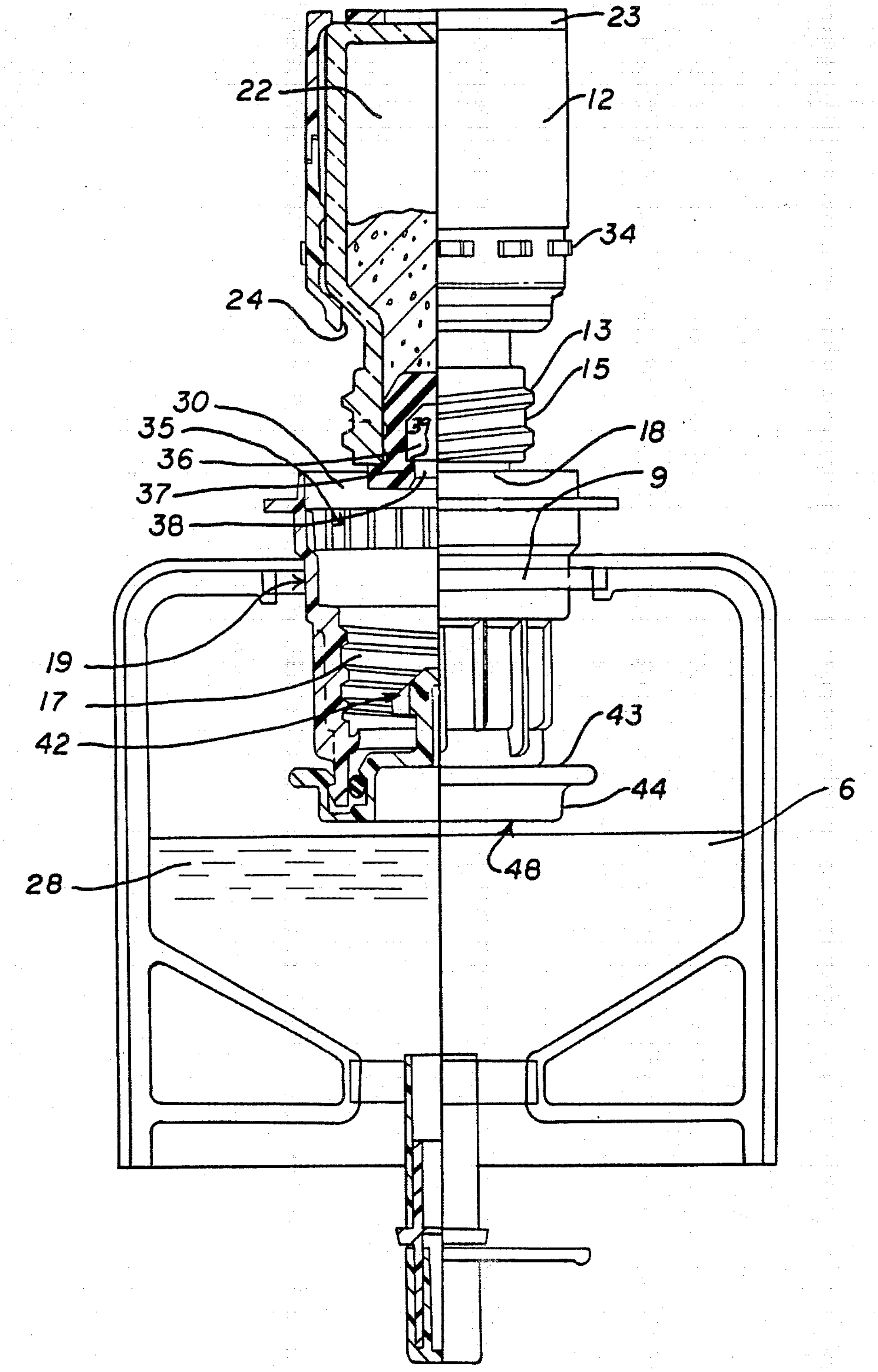
FIG. 1 is a front view, partially in section, of a flexible diluent container employing teachings of this invention and an aligned additive medicament vial before being secured to the flexible diluent container.

Proceeding to a detailed description of the illustrated embodiment of the invention, FIG. 1 illustrates an additive medicament vial 12 just prior to being secured to the flexible diluent container 6. The diluent container typically is supplied with a protective cap over the outer end of the port, see for example the closure disclosed in the copending application of Larkin, Tripp and Ziegler, Ser. No. 806,782, filed Dec. 9, 1985 assigned to the assignee of this invention, the disclosure of which is incorporated herein by this reference. Such a closure is not shown in FIG. 1, it being assumed that the port has been opened by the health care technician in preparation for engagement of the vial. As previously indicated, the additive medicament vial will be supplied independently of the flexible container with the interconnection being effected, for example, by the health care technician. Typically the medicament vial is supplied with a stopper 18 in the vial opening 9 and a removable, cap covering the stopper for maintaining sterility as described in U.S. Pat. No. 4,614,515. The cap is attached to a skirt member 21 which is circumscribed by a ring of ratchet teeth 34. A shroud 23 covers the lower portion of the vial. A label L overlaps the skirt and the shroud. The neck and discharge end portion 15 of the vial is exposed for engagement with the diluent container by tearing off the cap along an annular tear line at 24, as described in said U.S. Pat. No. 4,614,515. Once the cap is removed the vial may be inserted into the port 30 of the flexible container 6 with the ring of ratchet teeth 34 engaging complementary teeth 35 on the port to prevent easy removal of the vial.

Vial 12 has the usual end portion 15 with threads 13 extending therefrom. Complementary threads 17 extend internally from port 30 which is mandrel sealed at 19 to the walls of the flexible container 6. The stopper 18 is formed with a recess 36 with an annular lip or flange 37 defining an entrance throat 38 of reduced diameter and an annular internal shoulder 39 on its back or inward side.

When it is desired to mix the contents 22 of a vial 12 into a solution container 6, the caps are removed from the vial and the outer end of the port, and the vial and solution container components are brought into mating alignment as in FIG. 1. Then the vial 12 is screwed into port 30 resulting in the recess 36 of vial stopper 18 fitting over the engagement portion 42 of the port plug 48. The contents of vial 12 and the contents 28 of a flexible container 6 may then be mixed by dumping the contents of vial 12 into the container 6, by removing the port plug-engaged stopper combination. This is accomplished by manually pulling on the rim 43 of the cover portion 44 of the plug by manipulation from the exterior of the flexible bag 6, i.e., through the flexible container walls, as described further in the aforementioned patents.

Figure 2:
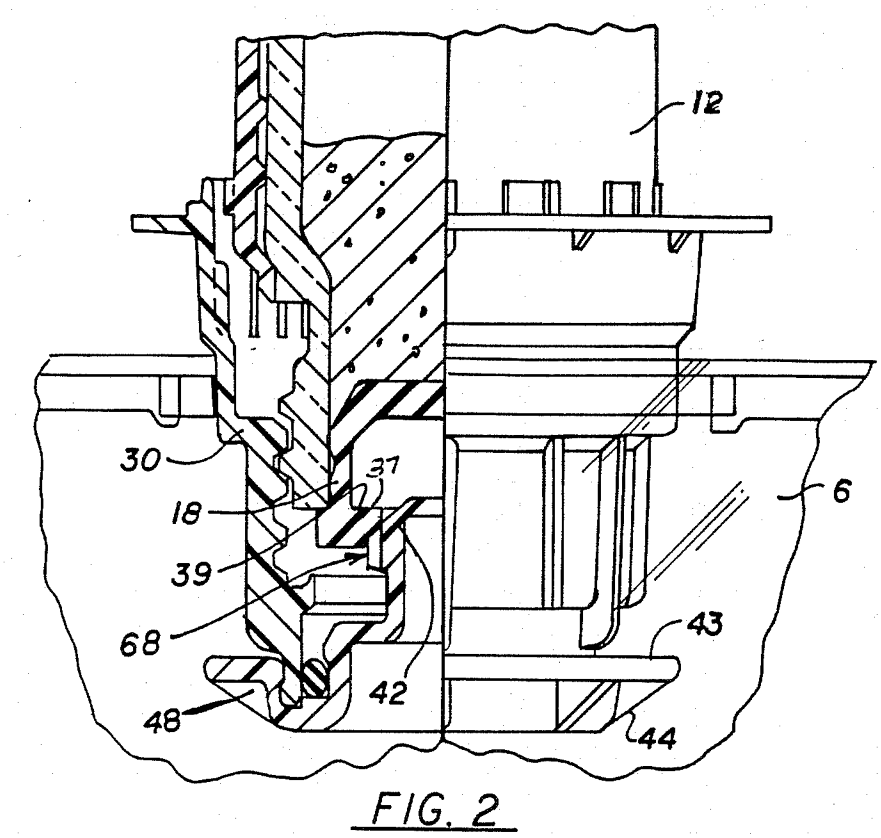
FIG. 2 is an enlarged partial view similar to FIG. 1 as the vial is being engaged with the flexible container.
Figure 3:
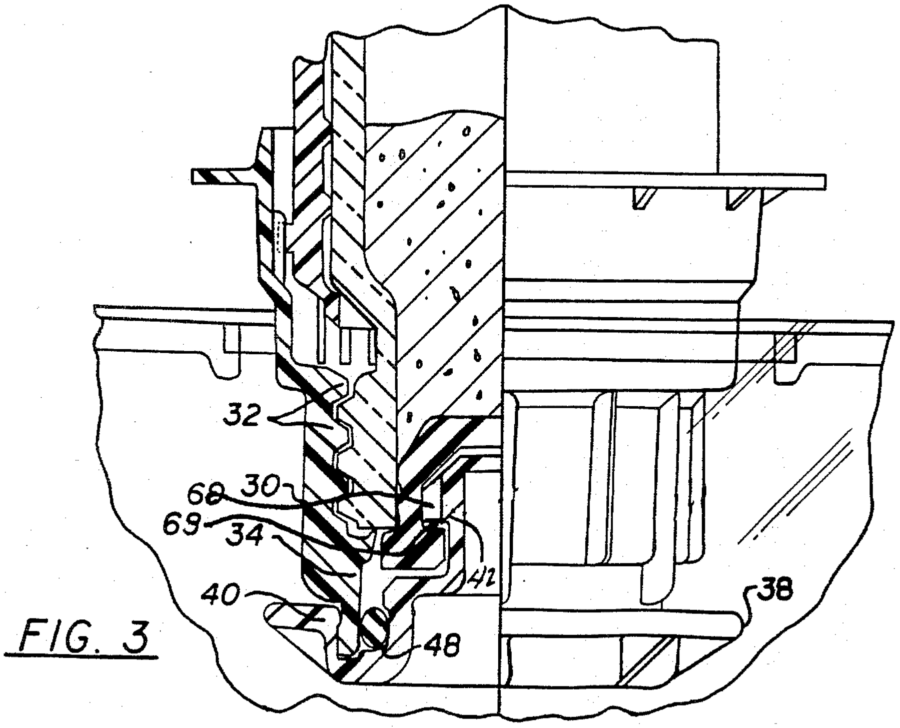
FIG. 3 is a view similar to FIG. 2 showing the vial fully engaged, with the port plug of the flexible container seated in the recess of the stopper.

FIG. 2 is an enlarged partial view of the engagement of the vial stopper of the additive container and the port plug of the flexible diluent container as the vial is being inserted into the port 30. In the particular design of this embodiment the engagement portion or extractor 42 of the plug 48 includes a head 45 and vanes or wings 68 supported on a stem 70 (see also FIG. 4) The vanes or wings 68 of the port plug, being angled, flexible and canted, tend to fold in toward the central axis of the extractor as the vial and stopper are rotated onto the engagement portion 42 of the port plug 48. This is illustrated in FIG. 2 where the leading edge of stopper 18 is inserted approximately halfway into port 30. The vanes need not flex or fold in all instances. Since they are narrow in width and tapered they provide minimal resistance to axial movement through the throat 38. Once the vial stopper is fully seated, as is shown in FIG. 3, the vanes 68 open up (if previously folded) and the proximal edges define a lateral shoulder on the inward side of the flange 37 thus providing good interference gripping on the lateral shoulder 39 of the stopper when the user wants to manipulate the bag and pull the port plug-stopper combination from the seated, sealing position of FIG. 3.

Figure 4:
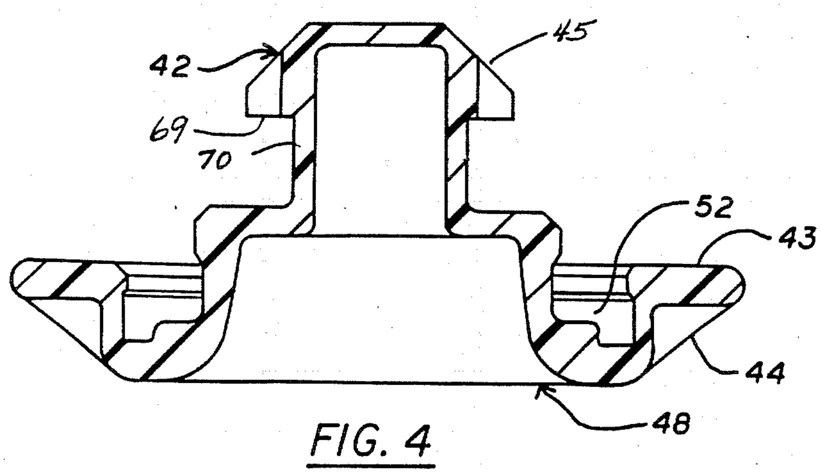
FIG. 4 is a center sectional view of the port plug of the embodiment of FIG. 1.

FIG. 4 depicts a sectional view of the vial port plug. An annular recess 52 is provided in port plug 48 to receive the inner annular end of the port 30 and an O-ring seal as seen in FIGS. 1, 2 and 3. A lip at the inner edge of rim 43 effects retentive latching engagement with a similar lip on the port; see FIGS. 2 and 3. The engagement or extractor portion 42 of the port plug 48 is tapered from a minimum diameter smaller than the diameter of throat 38 to the outer ends of the vanes to facilitate and ease movement through the resilient throat by pressing outward the engaged portions of lip 37. This enables engagement portion 42 to easily enter recess 36 of vial stopper 18. The stopper 18 is rotated onto the head 45 as the vial 12 is rotated into the threads 17 by virtue of the frictional engagement of the stopper in the vial neck. The head 45 of the engagement portion 42, above stem 70, may be larger in diameter than throat 38 of stopper 18. The vanes 68 extend radially outward from the head but each is narrow in width to facilitate their passage through throat 38 of stopper 18. The vanes may also flex or fold as a result of the relative rotary movement to reduce their effective radial length or diameter, and thereby further ease passage through the throat 38, particularly when the stopper 18 is composed of firmer less flexible materials. The outer diameter dimension across the proximal edges of the vanes is approximately equal to the diameter of the recess 36 inward of the lip 37, see FIG. 3.

Figure 5:
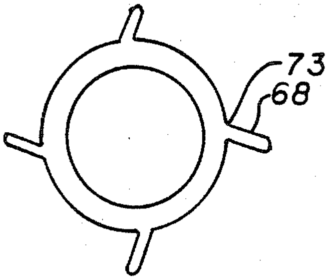
FIG. 5 is a top view of the extractor portion of the port plug of FIG. 4, with four canted engagement vanes.
Figure 6:
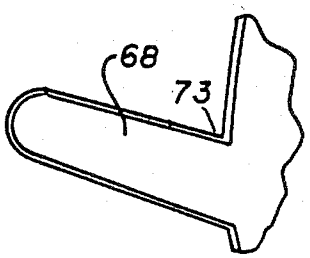
FIG. 6 is an enlarged fragmentary top view of one vane of the port plug of FIG. 4.

FIG. 5 is a top view of the extractor portion of the port plug 48, illustrating the disposition of the vanes 68. A number of parameters can be varied in regards to the design of the port plug including the number of vanes, thickness of the vanes, angle or cant of the vanes, draft angle or taper of the vanes, and the diameter of the head of the port plug itself. Currently, the preferred embodiment of the port plug is the four vane version as illustrated in FIG. 5. Here each vane 68 extends generally radially from the plug with the four vanes at 90° spacings. In one illustrative example, each individual vane is canted at an angle of about fifteen degrees toward the direction of rotation of the vial relative to the stopper, and the thickness of each vane is about 0.017" as measured at the base 73. Each vane extends about 0.55" radially from a head about 0.322" in diameter at the base of the vanes for engaging stoppers having a throat about 0.282" in diameter, a recess about 0.362" in diameter and a lip flange about 0.100" thick. Those vanes have a flexibility modulus in accordance with ASTM-790 of 145,000 psi. The outer end of the head 45 and vanes 68 have a conical taper of 45° relative to the axis of the extractor portion 42. FIG. 6 is an enlargement illustrating the detail of an individual wing 68 of the port plug. Here the wing is shown to taper in thickness with a draft angle of about 1° on each side surface.

Figure 7:
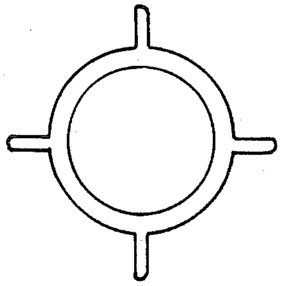
FIG. 7 is a top view of an alternate four-vane design of the extractor portion.
Figure 8:
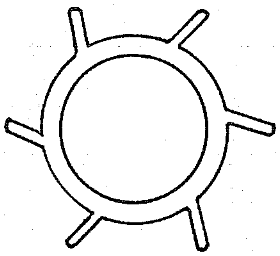
FIG. 8 is a top view of a six-vane design of the port plug.
Figure 9:
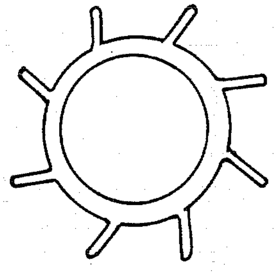
FIG. 9 is a top view of an eight-vane design of the port plug.

FIGS. 7–9 illustrate certain alternative embodiments of the port plug. FIG. 7 depicts a four vane straight radial port plug. Here the vanes are not canted. FIG. 8 illustrates a six vane port plug with the vanes at 60° spacings. In this embodiment the vanes are canted e.g., at an angle of about 15°. FIG. 9 similarly illustrates an eight vane version of the port plug with the vanes extending out from the central stem at the 45° positions. In each embodiment it is contemplated that the distal edge of each vane is tapered generally as in the embodiment of FIGS. 1–4.

OPERATION

After the closure is removed from a diluent container 6 and the end cover is removed from a selected vial 12, the vial is ready to be inserted into the flexible container 6 as shown in FIG. 1. In this position the medicament vial 12 is ready to be screwed into the port 30. The interengagement of vial 12 and port 30 is accomplished by threadable engagement of threads 13 with complementary threads 17 within port 30. Rotating vial 12 with respect to the flexible container 6 causes end 15 to be drawn into port 30. This drawing action causes engagement portion 42 of the port plug 48 to enter the recess 36 in stopper 18 as well as effecting sealing engagement of the vial with the port. As the vial 12 is screwed into port 30 the vanes of the port plug may fold in toward the axis of the extractor, particularly if the stopper is formed of firm material, thus allowing the initial engagement to be made without greatly increasing the amount of axial insertion force required. This can be seen in FIG. 2. When engagement portion 42 has completely entered recess 36, Wings 68 form a shoulder 69 (FIG. 4) at right angles to the axis, over the shoulder 39 of the stopper, thus fully and positively engaging the stopper. The ratchet teeth 34 engage the compatible ratchet teeth 35 in the port, thus preventing the vial 12 from being easily backed out of port 30 once interengagement has begun. With the port plug 48 fully seated as is shown in FIG. 3 a great amount of force is required to disengage the port plug 48 from the stopper 18. This ensures that the stopper 18 will be removed from the vial 12 when the port plug is removed from the port 30 by manually manipulating the cover 44 from the exterior of the flexible container 6 without the stopper and port plug becoming disengaged from one another.

This removal of the port plug 48 and stopper 18 combination will create an open path through vial opening 9 for medicament 22 to intermix with diluent 28. Diluent 28 and medicament 22 may be further intermixed by squeezing the sides of the flexible container 6.

Certain alternative embodiments of extractor portions for use in the invention are shown in FIGS. 7–9. The interconnecting of vial 12 into port 30 is substantially the same with these embodiments as previously described with respect to FIGS. 1–6. The preferred material for the port plug is a polypropylene copolymer.

The invention has been described as used in one particular system. Activation of the drug delivery system including the mixing of the medicament and diluent by removal of the port plug-stopper combination may be readily accomplished by health care or pharmacy personnel without the use of specially designed components or sophisticated methods which require an excessive number of procedures or prolonged exposure which might jeopardize sterility. It will be appreciated that the invention may be embodied in other similar systems.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

What is claimed is:

1. A flexible diluent container including an access port having first means for engaging the outlet portion of a second container which is closed by a removable stopper formed of resiliently compressible material and having an end wall of substantial thickness with a throat opening therethrough and an internal recess therewithin defining an inwardly facing shoulder inward of said end wall, said flexible container including extractor means comprising a protuberant engagement portion extending along a first axis for engaging such a stopper within said recess thereof for removal of the stopper from such a second container when engaged with said first means, wherein said engagement portion comprises a plurality of narrow vanes each joined with said protuberant engagement portion along said first axis and extending generally radially outward relative to said first axis such that their radially distal edges collectively define a transverse dimension of said engagement portion greater than the corresponding transverse dimension of said opening and said vanes are spaced from one another at said distal edges substantially greater distances than the thickness of said edges for ease of forcible passage through said throat and into said recess, said vanes having lateral axially proximal edges for thereafter engaging the internal shoulder of the stopper for effecting removal of said stopper from such a second container by said extractor means after entry into the recess of such a stopper.

2. The invention as defined in claim 1 wherein said port includes an inner end disposed inwardly of said diluent container and said extractor means is affixed to a cover which closes the inner end of said port and extends from said cover into said port.

3. The invention as in claim 1 in which said first means includes means in said port for engagement of such a vial by rotation of such vial relative to said port and said vanes are canted in the direction of such relative rotation.

4. The invention as defined in claim 1 wherein said vanes are canted relative to the respective radii.

5. The combination of a vial which has a removable stopper with a recess in an exposed end thereof, said recess including a throat portion, an inner portion of larger cross-section than said throat portion and defining a shoulder on the inward side of said throat portion, and a port plug with extractor means including a protuberant engagement portion extending along a first axis for engaging said stopper within said recess for removal of said stopper from said vial, wherein said protuberant engagement portion of said port plug comprises a plurality of narrow vanes each joined with said protuberant engagement portion along said first axis and extending generally radially outward relative to said first axis such that their radially distal edges collectively define a transverse dimension of said engagement portion greater than the corresponding transverse dimension of said throat portion and said vanes are spaced from one another at said distal edges for ease of forcible passage through said throat portion into said recess, said vanes being tapered at their distal edges to facilitate entry into the recess of such a stopper and having lateral axially proximal edges for thereafter engaging the shoulder of the stopper for effecting removal of said stopper by said extractor means.

6. The invention as defined in claim 5 wherein said extractor means is affixed to a cover for closing a port opening spaced from said vial.

7. A port plug with extractor means including an engagement portion extending along a first axis for engaging a stopper within a recess in the exposed end of the stopper, and which stopper has an access opening to said recess and an internal annular shoulder in such recess, for removal of such stopper from a vial, wherein said engagement portion of said port plug comprises a plurality of narrow vanes each joined with said protuberant engagement portion along said first axis and extending generally radially outward relative to said first axis such that their radially distal edges collectively define a transverse dimension of said engagement portion greater than the corresponding transverse dimension of said access opening and said vanes are spaced from one another at said distal edges substantially greater distances than the thickness of said edges for ease of forcible passage through said access opening and into said recess, said vanes being tapered at their distal edges to facilitate entry into the recess of such a stopper and having lateral axially proximal edges for thereafter engaging the shoulder of the stopper for effecting removal of said stopper by said extractor means.

8. The invention as in claim 7 wherein said vanes are flexible for resilient bending about said first axis.

9. The invention as in claim 1 wherein the vanes are tapered at their distal edges to facilitate entry into the recess of such a stopper.

10. The invention as in claim 1 wherein each of said vanes has a thickness of about 0.017 inches.

11. The invention as in claim 1 wherein said vanes are flexible for resilient bending about said first axis.

12. The invention as in claim 3 wherein said vanes are flexible for resilient bending about said first axis.

13. The invention as in claim 7 wherein said vanes are flexible for resilient bending about said first axis.

* * * * *